United States Patent [19]

Lipton

[11] Patent Number: 4,891,501
[45] Date of Patent: * Jan. 2, 1990

[54] THERAPEUTIC TREATMENT PAD

[76] Inventor: Barry Lipton, 11433 Flints Grove La., Gaithersburg, Md. 20878

[*] Notice: The portion of the term of this patent subsequent to May 10, 2005 has been disclaimed.

[21] Appl. No.: 180,458

[22] Filed: Apr. 12, 1988

Related U.S. Application Data

[63] Continuation-in-part of Ser. No. 909,332, Sep. 19, 1986, Pat. No. 4,742,827.

[51] Int. Cl.⁴ .............................................. H05B 3/06
[52] U.S. Cl. .................................... 219/527; 219/528; 219/529; 128/380
[58] Field of Search ............... 219/527, 528, 548, 549, 219/241, 535, 529; 128/380, 379, 384, 385, 399, 402, 403

[56] References Cited

U.S. PATENT DOCUMENTS

| | | | |
|---|---|---|---|
| 551,939 | 12/1895 | Weber | 128/403 |
| 723,797 | 3/1903 | Williams | 128/379 |
| 1,594,053 | 7/1926 | Evans | 128/379 |
| 2,071,706 | 2/1937 | Reach | 128/380 |
| 2,429,583 | 10/1947 | Ogle | 128/380 |
| 3,839,621 | 10/1974 | Hariu | 219/527 X |
| 3,889,684 | 6/1975 | Lebold | 128/403 |
| 4,061,897 | 12/1977 | Thykeson | 219/527 X |
| 4,512,830 | 4/1985 | Hulett et al. | 128/380 |

Primary Examiner—B. A. Reynolds
Assistant Examiner—M. Lateef
Attorney, Agent, or Firm—Oblon, Spivak, McClelland, Maier & Neustadt

[57] ABSTRACT

A therapeutic pad includes a flexible member including a flat and substantially rectangular central portion defining ends spaced in the direction of elongation of the central portion and sides spaced in a direction transverse to the direction of elongation. A substantially semi-circular cut-out is provided in the central portion, the cut-out extending from an intermediate portion of one of the sides towards the other of the sides. A flat substantially rectangular extending portion projects from one side adjacent each of the ends in a direction substantially transverse to the direction of elongation of the central portion. Straps or other such means are provided for selectively connecting the opposite ends while a heating or cooling element may be positioned within the pad.

13 Claims, 6 Drawing Sheets

THERAPEUTIC TREATMENT PAD

The present application is a continuation-in-part of U.S. patent aplication Ser. No. 909,332, filed on Sept. 19, 1986 and now U.S. Pat. No. 4,742,827.

BACKGROUND OF THE INVENTION

1. Field of the Invention

The present invention relates to a therapeutic treatment pad, and more particularly to a pad for providing bilateral cold or moist heat treatment of at least three related muscle groups.

2. Description of the Related Art

It is well known that cold or heat, and in particular moist heat, can be used in the therapeutic treatment of injured muscles. It has also been known that muscle injuries often occur simultaneously in muscles which comprises a group for performing a given task. For example, the Temporalis (Temporoparietalis and Auriculares), together with the Masseter, Pterygoid and Hyoid muscles operate as a group in mastication and are sometimes injured as a result of trauma in automobile accidents. Effective therapeutic treatment of these muscles requires that bilateral treatment, either with cold or moist heat, of all the muscles of this group be performed simultaneously.

Similarly, the muscles of the upper back, rear shoulder and neck form a group used in flexure of these areas of the body and may be injured during "whiplash". These muscles, i.e., the Mylohyoids, upper Trapezius, Sternocleidomastoid and the Insertion of the Internal Pterogoid, should also receive bilateral simultaneous therapeutic treatment.

Yet another group of muscles requiring simultaneous bilateral treatment is used in the flexure of the neck and chest, and include the upper cervical, the upper ends of the Trapezius, the lower portion of the Sternocleidomastoids and the upper Pectoralis. This third group is also sometimes injured during "whiplash" in a vehicle accident.

Moist heat treatment pads are well known. An example is the "Hydrothero Pad" manufactured by Roberts Manufacturing Company of Baltimore, Md. For the treatment of the above groups of muscles, Roberts manufactures an essentially rectangular pad. However, the rectangular pad is incapable of adequately covering any individual muscle group, or of simultaneously moist heat treating all of the muscles of each of the above groups without uncomfortable binding or "cuffing" of the pad against areas to be treated.

SUMMARY OF THE INVENTION

It is an object of the present invention to provide a therapeutic treatment pad capable of being comfortably and safely positioned in at least three positions wherein all of the muscles of a given group are simultaneously and evenly treated.

According to the invention, the therapeutic pad includes a flexible pad member including a flat, substantially rectangular central portion defining ends spaced in the direction of the elongation of the central portion, and sides spaced in a direction transverse to the direction of elongation. A cut-out is provided in the central portion, the cut-out extending from an intermediate portion of one of the sides towards the other of the sides. Substantially rectangular extending portions extend from the one side adjacent each of the ends of the pad and in a direction substantially transverse to the direction of elongation of the central portion. Means, such as straps, are provided for selectively and securely connecting the opposite ends. In the case of a heating pad, means such as a heat retentive mass or electric heating filaments, are provided in the pad for heating the same. The heating means are shaped so as to be able to evenly heat the entirety of the pad member. In the case of a cold treatment pad, cooling means in the pad can be a cold retention mass or a chemical coolant.

The so shaped pad is sized so as to be able to simultaneously therapeutically treat all muscles of at least the first, (mastication) group when in a first position, all muscles of the second (neck and back) group when in a second position and all muscles of the third (neck and chest) group when in a third position.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
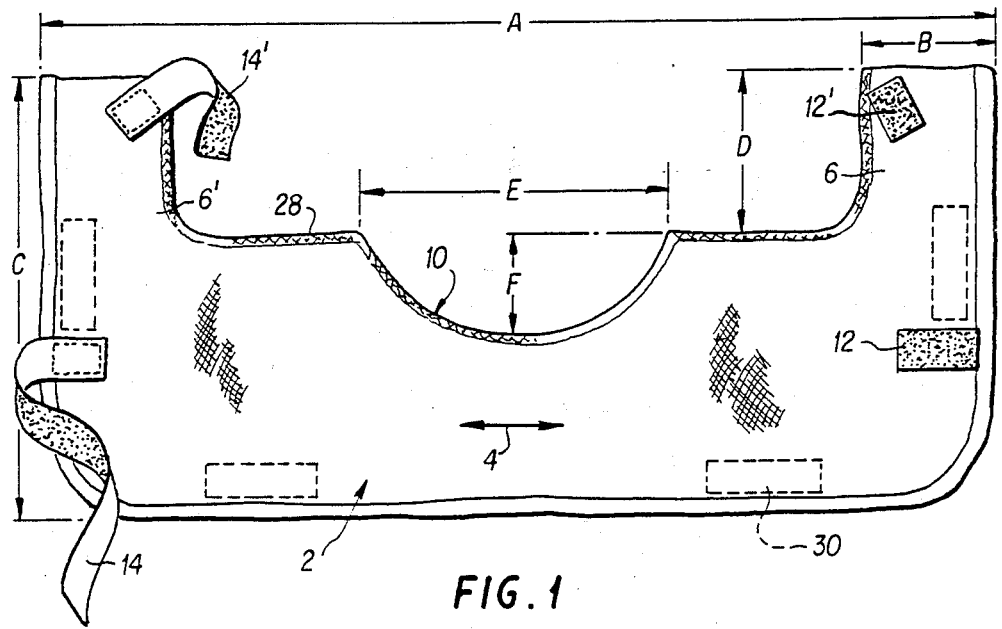
FIG. 1 is a plan view of a first embodiment of a pad of the invention.

A therapeutic pad according to the invention will now be described with reference to the accompanying Figures, wherein the same or corresponding reference numerals are used to identify the same or corresponding parts throughout the several views.

The general shape of a first embodiment of the invention is shown in plan in FIG. 1. It includes an elongate rectangular central portion 2 having a direction of elongation shown by arrows 4, and a pair of substantially rectangular extending portions 6 and 6' which extend from the ends of the central portion in a direction transverse to the direction of elongation. The side of the central portion between the extending portions 6 and 6' is provided with a generally semi-circular shaped cut-out 10. Velcro pads 12 and 12' are attached to one end of the central portion and to the extending portion 6, while straps 14 and 14' having Velcro (trademark for hook and loop type fabric connector) thereon are respectively fixed to the opposite end of the central portion and to the extending portion 6'. The straps 14 and 14' comprise means for selectively connecting the opposite ends of the central portion to one another and to the extending portions.

Figure 2:
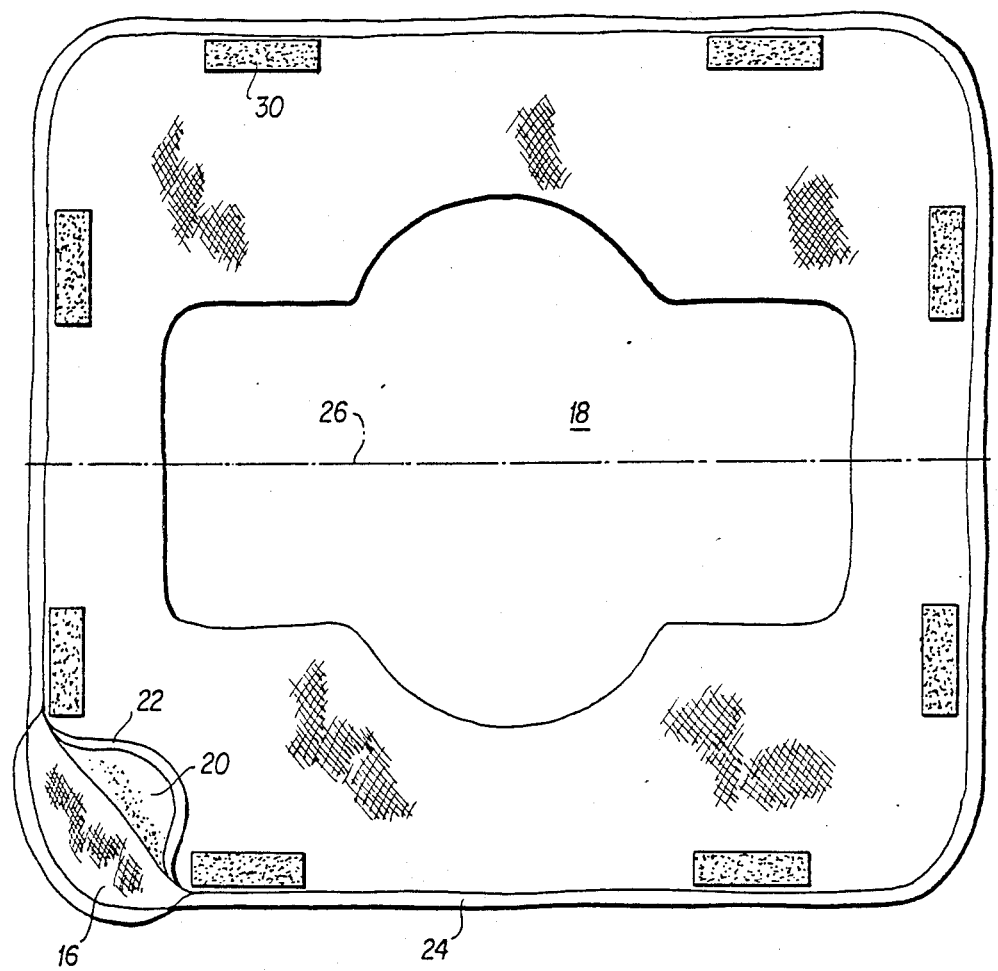
FIG. 2 shows the first embodiment in an intermediate state of manufacture.

The pad of FIG. 1 is made by folding a laminated pad preform having the shape shown in FIG. 2. In FIG. 2, a first layer 16 of soft cloth or other flexible material, such as terrycloth, has a substantially square or rectangular shape and is provided with a central opening 18. An intermediate layer 20 of soft absorbent material, such as lamb's wool, is laid on the bottom layer 16. An upper layer 22, which may also be formed of terrycloth, is then laid on the laminate of the bottom layer 16 and the intermediate layer 20. The outer peripheral edges of the layers 16, 20 and 22 are then sewn together, optionally with the use of reinforcement strip 24.

The opening 18 may be formed in each of the layers prior to assembly of the laminate, or may be cut in the assembled laminate. Similarly, the exterior periphery of the layers of the laminate may be cut prior to assembly, or the laminate may be assembled and then cut for final sizing.

The pad preform is then folded along line 26 to result in the pad having the shape shown in FIG. 1. The two halves of the folded pad preform are sewn about the entire periphery of the opening 18 to form a sewn seam 28 in the folded pad. The two halves of the resulting pad are held together about the remainder of their periphery by Velcro strips 30, as a result of which the halves of the pad can be separated at the strips 30 for the insertion of a heat retentive mass. The Velcro strips can then be resealed so as to retain the heat retentive mass.

The heat retentive mass, which is not shown, may be conventional, except in shape. For example, it can be in the form of a textile bag filled with wet heated sand. The bag should be shaped so that it is capable of providing heat to the entirety of the pad, including the rectangular extending portions 6 and 6'. For example, the bag containing the heat retentive material can also have the shape of an elongate rectangle having rectangular extending portions and a cut-out, as shown in FIG. 1.

Figure 3:
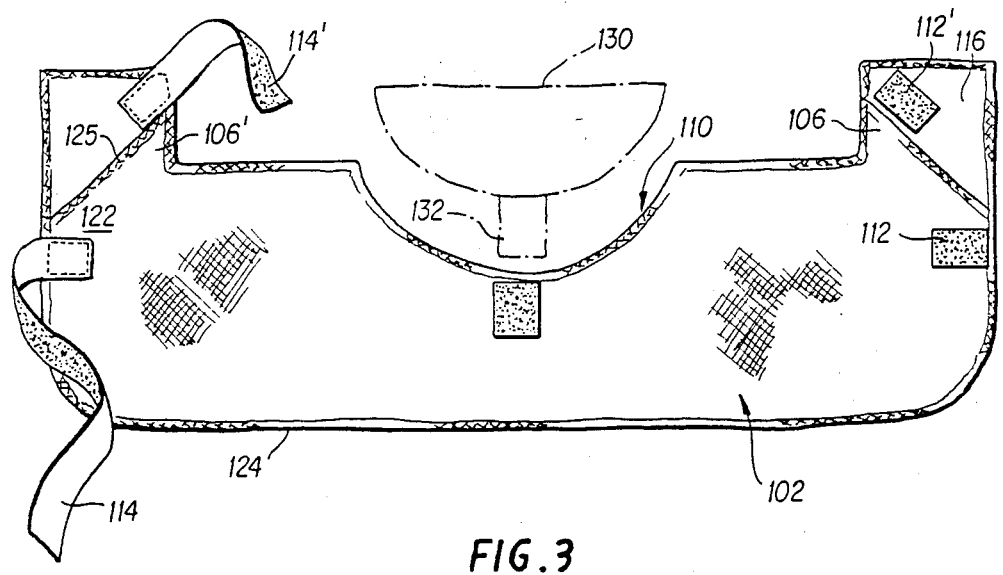
FIG. 3 is a plan view of a second embodiment of a pad of the invention.

The second embodiment of FIG. 3 includes an elongate central portion 102, rectangular extending portions 106 and 106', and a cut-out 110, and has an overall shape similar to that of the first embodiment. The second embodiment is used with an electrical heating element. It is formed of two layers of lamb's wool sewn along their periphery by stitches 124. The bottom layer 116 has fully extending rectangular extending portions, while the rectangular extending portions of the upper layer 122 terminate at edge 125 which is not sewn to the lower layer 116. As a result, an electrical heating element can be inserted between the layers 116 and 122 by insertion at the edge 125. The electrical heating element is preferably a flexible plastic bag having heating nichrome heating wires therein and shaped so as to extend into the extending portions 106 and 106'. Alternatively the electrical heating element can be permanently sealed in the pad. Velcro pads 112 and 112' cooperate with Velcro covered straps 114 and 114' for securement of the ends of the pad to one another during use.

Shown in dashed lines in FIG. 3 and provided with reference numeral 130 is an optional neck flap which may be connected to the cut-out 110 by strap 132.

Figure 4:
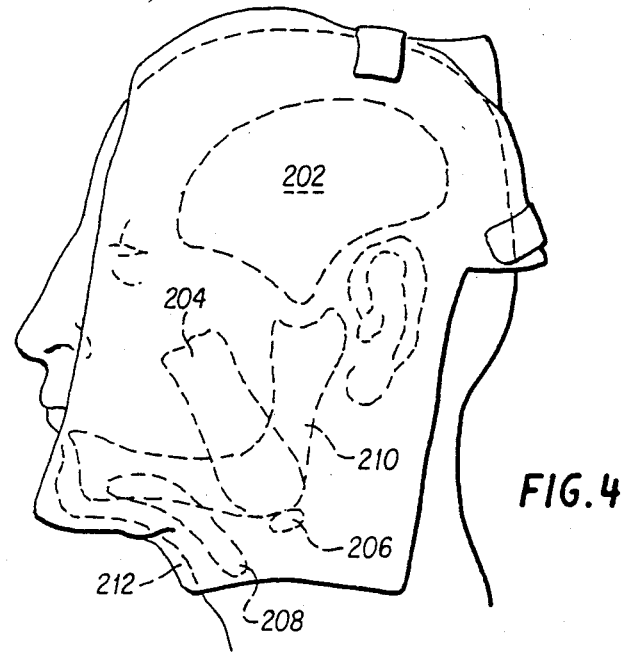
FIG. 4 shows the pad of the invention applied to the mastication group muscles.

A preferred use of the therapeutic pad according to the invention will now be described:

FIG. 4 shows the first or mastication muscle group with a pad of the invention superimposed thereon in dashed lines. As can be seen, the pad is applied with the cut-out 10 circling the front half of the neck, the portions of the central portion 2 on either side of the cut-out being draped upwardly on either side of the head and the rectangular extending portions 6 and 6' extending rearwardly toward one another at the upper back of the head. The straps 14 and 14' are attached to the corresponding Velcro strips 12 and 12'. As can be seen, the Temporalis 202, Massiters 204, Insertion of the Internal Pterygoid 206 and Hyoid muscles 208 are all covered by the pad. Element 210 is the jawbone. The provision of the cut out 10 permits the pad to be positioned sufficiently posteriorally so that the extending portions 6 and 6' fully cover the Temporalis without the pad binding against the neck at 212 the Temporalis and hindering swallowing or breathing. The pad contains a moist heat retentive mass, and so applies wet therapeutic heat treatment to all of the first group muscles.

Figure 5:
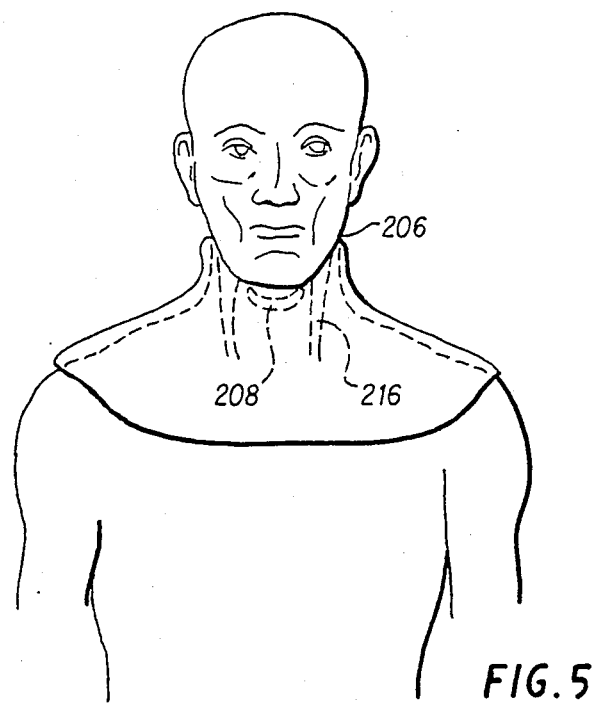
FIG. 5 is a posterior view of a pad of the invention applied to the back and neck group muscles.
Figure 6:
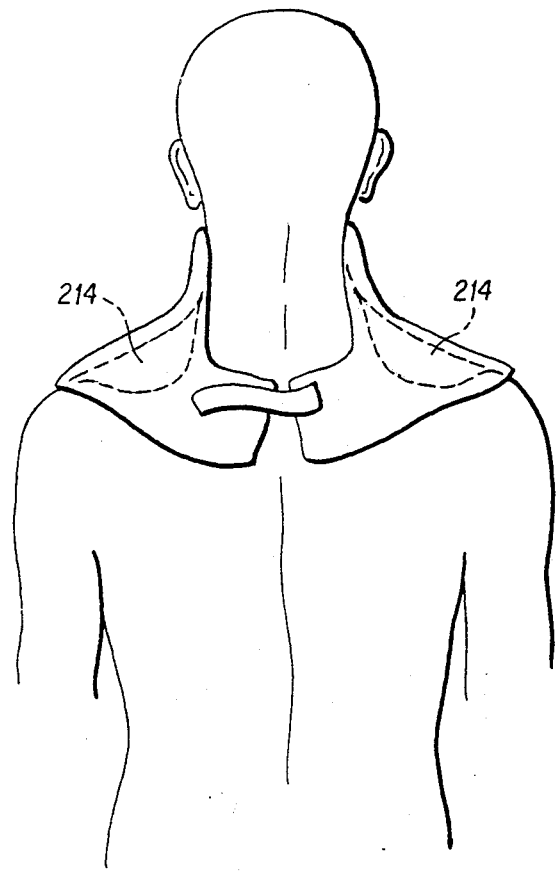
FIG. 6 is a anterior view of the pad in the position of FIG. 5.

For the application of therapeutic heat to the second group of back and neck muscles, the pad is positioned as shown in FIGS. 5 and 6. As can be seen from the Figures, the cut-out 10 permits extending portions 6 and 6' to drape around the back and cover the upper Trapezius 214 while at the same time the central portion 2 of the pad fits about the neck and comfortably covers the Sternocleidomastoid 216, the Insertion of the Internal Pterogoid and the Molyhyoids without tightly binding and without impeding respiration and swallowing. It may be appreciated that without the cut-out 10 the central portion 2 would either cuff at the neck and restrict breathing or the extending portions would not cover the upper Trapezius.

Figure 7:
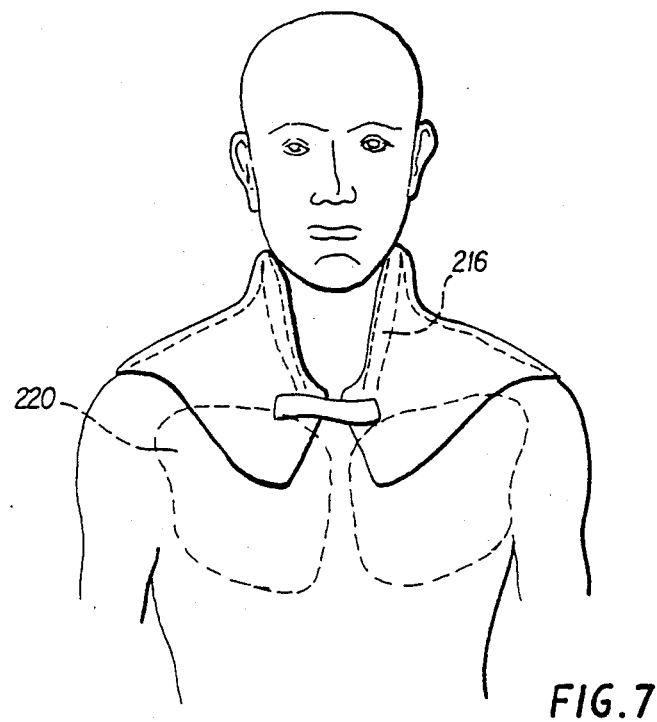
FIG. 7 is an anterior view of a heating pad of the invention applied to the neck and chest group muscles.
Figure 8:
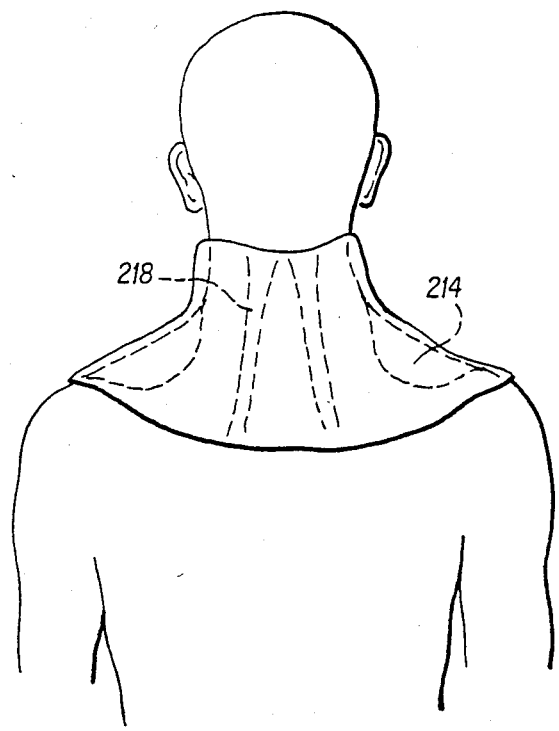
FIG. 8 is a posterior view of the pad in the position of FIG. 7.

The third position for applying therapeutic treatment to the third group of muscles of the neck and chest is shown in FIGS. 7 and 8. As seen in FIG. 7, the additional length provided by the extending portions 6 and 6' permit them to drape over the chest to cover both the upper end of the Trapezius 214, the Cervical 218 and the upper Pectoralis 220. The cut-out 10 again permits the pad to comfortably conform to the neck such that the Sternocleidomastoid is covered.

Accordingly, it may be appreciated that all three muscle groups may be therapeutically treated by a single pad due to the unique shape thereof including features which accommodate the body configurations in a novel and unexpected manner, these features including the flat and substantially rectangular central portion having a cut-out, together with the extending portions extending from the ends of the rectangular portion.

Preferred, but not limiting, dimensions of the pad are:

| | |
|---|---|
| A - 23 in. | D - 4 in. |
| B - 3.5 in. | E - 6 in. |
| C - 10.5 in. | F - 2.5 in. |

Although the above description refers to heat treatment, the pad described in the first two embodiments can also be used for therapeutic cold treatment by changing the heating means to a cold producing means, such as a bag containing a mass of cold retentive material, such as wet sand or a Bentonite and water mixture, or by using a bag containing a chemical coolant such as ammonium nitrate and water which undergoes an endothermal chemical reaction when mixed. A known pad using Bentonite is the "Cold Pac" made by the Chattanooga Corp. A known pad using ammonium nitrate and water is the Instant Cold Pack made by Woodlets Inc. of Buffalo, N.Y.

Figure 9:
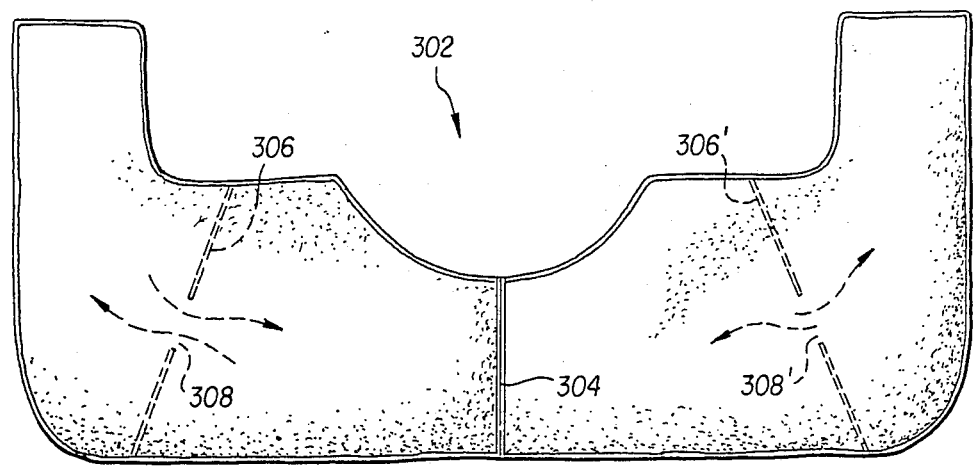
FIG. 9 is a plan view of a third embodiment of a pad of the invention used.

FIG. 9 is a plan view showing an embodiment of a pad according to the invention which is designed specifically for therapeutic cold treatment (but which also be used for hot treatment). The shape of the pad is the same as that in the first embodiments. The major difference is that the pad is preferably formed of a liquid impermeable material, such as vinyl plastic, the interior of which is divided as described below.

The pad 302 shown in FIG. 9 is preferably formed of two identically shaped sheets of vinyl or a similar flexible plastic material, which are heat sealed at their edges to define a sealed volume therein. A heat sealed division line 304 partitions the interior of the pad 302 into two symmetrical halves, so that, in the case of a pad using an ammonium nitrate and water mixture, only one half of the pad need be used at a given time.

Partial partitions 306 and 307 partially divide each of the halves into two segments, which communicate with each other only through a small opening 308 or 308' in the partitions 306 and 306'. For example, the openings can be formed by selectively heat sealing the pad only along a portion of the line defined by each partition.

In the case of a chemical coolant such as ammonium nitrate and water which requires cryogenic properties only upon mixing, the partitions 306 and 306' can control the rate at which the materials are mixed, and so can control the rate of cooling. For example, the pad may be filled with ammonium nitrate pellets and a sealed water bag may be positioned in one segment of each half. Upon breaking upon the water bag, water from the segment containing the bag will mix with the ammonium nitrate in the other segment at a controlled rate.

Obviously, numerous modifications and variations of the present invention are possible in light of the above teachings. It is therefore to be understood that within the scope of the appended claims, the invention may be practiced otherwise than an as specifically described herein.

What is claimed as new and desired to be secured by Letters Patent of the United States is:

1. A therapeutic treatment pad comprising:
 a flexible pad member including:
 (a) a flat, substantially rectangular central portion defining two elongate and substantially parallel sides extending along a direction of elongation and two ends shorter than said elongate sides and spaced in the direction of elongation of said central portion, said elongate sides being spaced in a direction transverse to said direction of elongation,
 (b) a concave cut-out in said central portion, said cut out extending from an intermediate portion of one of said sides towards the other of said sides,
 (c) flat extending portions projecting from said one of said sides adjacent each of said ends and in said direction substantially transverse to said direction of elongation of said central portion, said flat extending portions being spaced from said cut-out in said direction of elongation;
 means for selectively connecting opposite ones of said ends; and
 means for modifying the temperature of the entirety of said central portion of said pad member.

2. The pad of claim 1 wherein each of said extending portions is substantially rectangular and has an edge defining an extension of one of said ends of said central portion and extending away from said other of said sides of said central portion.

3. The pad of claim 1 wherein said means for modifying the temperature are positioned within said pad member.

4. The pad of claim 3 wherein said means for modifying the temperature comprises a heat or cold retentive mass having a shape corresponding to a shape of said pad member.

5. The pad of claim 3 wherein said means for modifying the temperature comprise at least one electric heating means sized and shaped as to be able to heat said pad member.

6. The pad of claim 3 wherein said pad member includes at least two layers, wherein said means for modifying the temperature is positioned between said layers.

7. The pad of claim 1 including means for selectively connecting each of said opposite ends to said extending portion projecting from the other of said opposite ends.

8. The pad of claim 7 wherein said means for selectively connecting said opposite ends comprise straps fixed to a least one of said ends.

9. The pad of claim 5 including a removable neck flap attached to said central portion adjacent said cut-out.

10. The pad of claim 1 wherein said pad member is sized and shaped to comprise means for simultaneously therapeutically treating all muscles of a first mastication group when in a first position, all muscles of a second neck and back group when in a second position and all muscles of a third neck and chest group when in a third position, wherein:
 (a) said first group comprise the Temporalis, Masseter, Insertion of the Internal Pterygoid and Hyoid muscles, bilaterally,
 (b) said second group comprises the Mylohyoid, Sternocleidomastoid, Insertion of the Internal Pterygoid and upper Trapezius muscles, bilaterally, and
 (c) said third group comprises the upper Cervicle, Trapezius, Sternocleidomastoid and upper portions of the Pectoralis muscles, bilaterally.

11. The pad of claim 6 wherein said means for modifying the temperature comprises cooling means.

12. The pad of claim 11 including a partition dividing the space between said two layers into two symmetrical and isolated halves.

13. The pad of claim 12 including means for partitioning each of said halves.

* * * * *